US005548843A

United States Patent [19]
Chase et al.

[11] Patent Number: 5,548,843
[45] Date of Patent: Aug. 27, 1996

[54] BACK SUPPORT WITH MEANS TO SECURE THE BELT ON THE WEARER WHILE IN AN OPEN POSITION

[75] Inventors: David D. Chase; Gary D. Shumate, both of Albuquerque, N.M.; Joel A. Joslin, Sunset Hills, Mo.; Paul K. Meunchen, Holland, Mich.

[73] Assignee: Chase Ergonomics Inc., Albuquerque, N.M.

[21] Appl. No.: 180,898

[22] Filed: Jan. 12, 1994

[51] Int. Cl.⁶ .................................................. A41D 13/00
[52] U.S. Cl. ........................................ 2/102; 2/93; 602/19
[58] Field of Search .................................. 2/44, 2, 92, 69, 2/311, 338, 322, 102, 16, 46, 92, 108; 602/19; 128/100.1, 101.1, 121.1, 96.1; 450/155; 66/19

[56] References Cited

U.S. PATENT DOCUMENTS

| | | | |
|---|---|---|---|
| 4,302,847 | 12/1981 | Miles | 2/2 |
| 4,833,730 | 5/1989 | Nelson | 2/44 |
| 5,052,052 | 10/1991 | Gilford et al. | 2/69 |
| 5,232,424 | 8/1993 | Pearson et al. | 2/338 |
| 5,257,419 | 11/1993 | Alexander | 2/44 |
| 5,351,340 | 10/1994 | Aldridge | 2/108 |

FOREIGN PATENT DOCUMENTS 2259848  3/1993  United Kingdom ........................ 2/338

OTHER PUBLICATIONS

Chase Ergonomics, "Lumbar-Lock Back Support With Shoulder Straps," Mar. 1992.

Primary Examiner—C. D. Crowder
Assistant Examiner—Gloria Hale
Attorney, Agent, or Firm—Polster, Lieder, Woodruff & Lucchesi

[57] ABSTRACT

A back support for a human user includes an elastic support belt having first and second free ends, members secured to the support belt for releasably joining the free ends for maintaining the belt in a closed position in which it forms a closed surface adapted to encircle a human user, and structure secured to the support belt for releasably maintaining the belt in an open position in which the support belt free ends are unattached to each other. A related back support garment includes a garment body having a garment front and a garment back defining an inside and an outside of the garment, the garment body being suitably sized for a human wearer. An elastic support belt is disposed inside the garment body and secured thereto. The elastic support belt has first and second free ends and also has structure for releasably joining the free ends for maintaining the support belt in a closed position in which the support belt forms a closed surface adapted to encircle the human wearer.

14 Claims, 7 Drawing Sheets

BACK SUPPORT WITH MEANS TO SECURE THE BELT ON THE WEARER WHILE IN AN OPEN POSITION

BACKGROUND OF THE INVENTION

This invention relates to back supports, and more particularly to a support belt useable by workers in a variety of occupations.

It is well known that the lifting of heavy objects can result in back injuries. Such injuries are even more likely to occur when the muscles supporting the back become fatigued, as can occur to truck drivers and the like as a result of the vibratory motion of the vehicle. In those circumstances, even the lifting of a lightweight object can cause injury to the back. It should also be appreciated that other workers also require back support while performing their regular tasks. For example, fire fighters and construction workers, as well as laboratory workers, barbers and hairdressers, could use additional back support in performing their daily jobs. Many of these workers are required to (or choose to) wear certain items of apparel (hereinafter generically referred to as garments) which might interfere with the wearing of a support device such as a belt. For example, fire fighters, laboratory technicians, doctors, nurses, barbers and hairdressers often wear coats or jackets while performing their jobs. Likewise, construction workers conventionally wear tool belts, reflective vests, and the like. Conventional back supports are not always readily useable with these items of apparel.

Back supports have been provided to protect a person's back from injury. One such back support is sold by Chase Ergonomics under the trade designation Lumbar Lock. This back support includes a support belt which removably wraps around the lower abdomen of a user and suspender-like shoulder straps which help prevent the support belt from sliding down during use. A pair of cinch straps are disposed over the support belt and are removably fastened together over the support belt. The support belt in combination with the cinch straps provide the desired back support. Although this back support performs its function quite well, it must be worn in a support mode at all times to maintain its proper position. The back support may become hot and uncomfortable to wear. Moreover, support belts may be considered by some people to be unsightly or inappropriate in appearance for certain workers such as lab technicians. In addition, it is inconvenient for some workers to wear a support belt in addition to their normal work attire, such as a lab coat, a barber's jacket, or the like. Therefore, present support belts could be improved.

SUMMARY OF THE INVENTION

Accordingly, one object of the present invention is to provide an improved back support which may be used by workers in a variety of occupations.

Another object is to provide such a support which may be worn in a supporting mode when back support is needed and in a relaxed mode when no back support is needed.

A third object is to provide such a belt which can provide additional lumbar support during use.

A fourth object is to provide a support belt which does not present an unsightly appearance.

A fifth object is to provide a support belt readily useable with a garment normally worn by a user.

These and other objects will become apparent to those skilled in the art upon a review of the following description and accompanying drawings.

Briefly, a back support of the present invention includes an elastic support belt having first and second free ends, structure secured to the support belt for releasably joining the free ends for maintaining the support belt in a closed position in which the support belt forms a closed surface adapted to encircle a human user, and structure secured to the support belt for releasably maintaining the belt in an open position in which the support belt free ends are unattached to each other.

A back support garment of the present invention includes a garment body having a garment front and a garment back defining an inside and an outside of the garment, the garment body being suitably sized for a human wearer. An elastic support belt is disposed inside the garment body and secured thereto. The elastic support belt has first and second free ends and structure secured to the support belt for releasably joining the free ends for maintaining the support belt in a closed position in which the support belt forms a closed surface adapted to encircle the human wearer.

BRIEF DESCRIPTION OF THE DRAWINGS

Similar reference characters indicate similar parts throughout the several views of the drawings.

DESCRIPTION OF THE PREFERRED EMBODIMENTS

Figure 1:
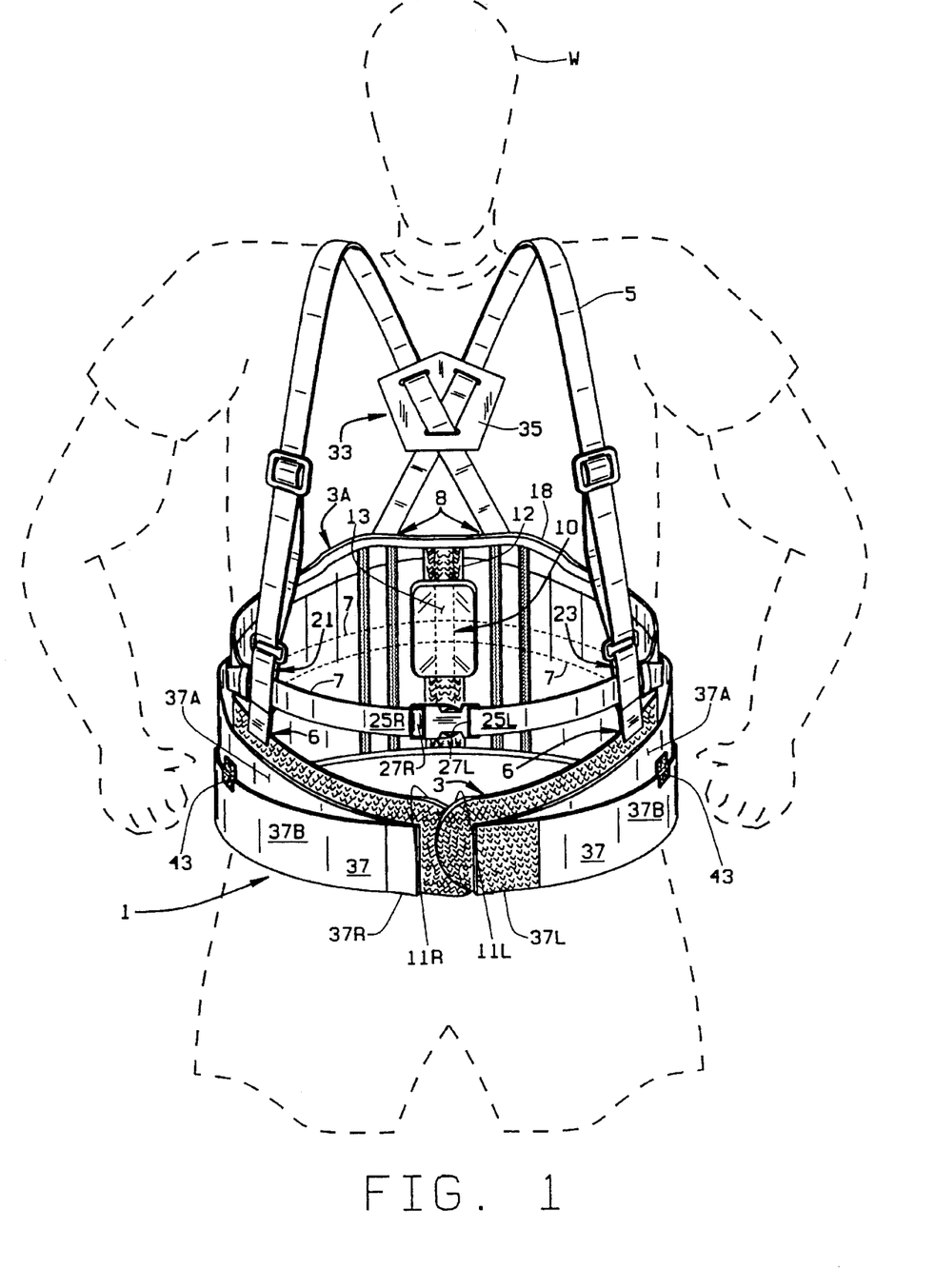
FIG. 1 is a perspective view of an illustrative embodiment of a back support in a closed position, a wearer being shown in position.
Figure 2:
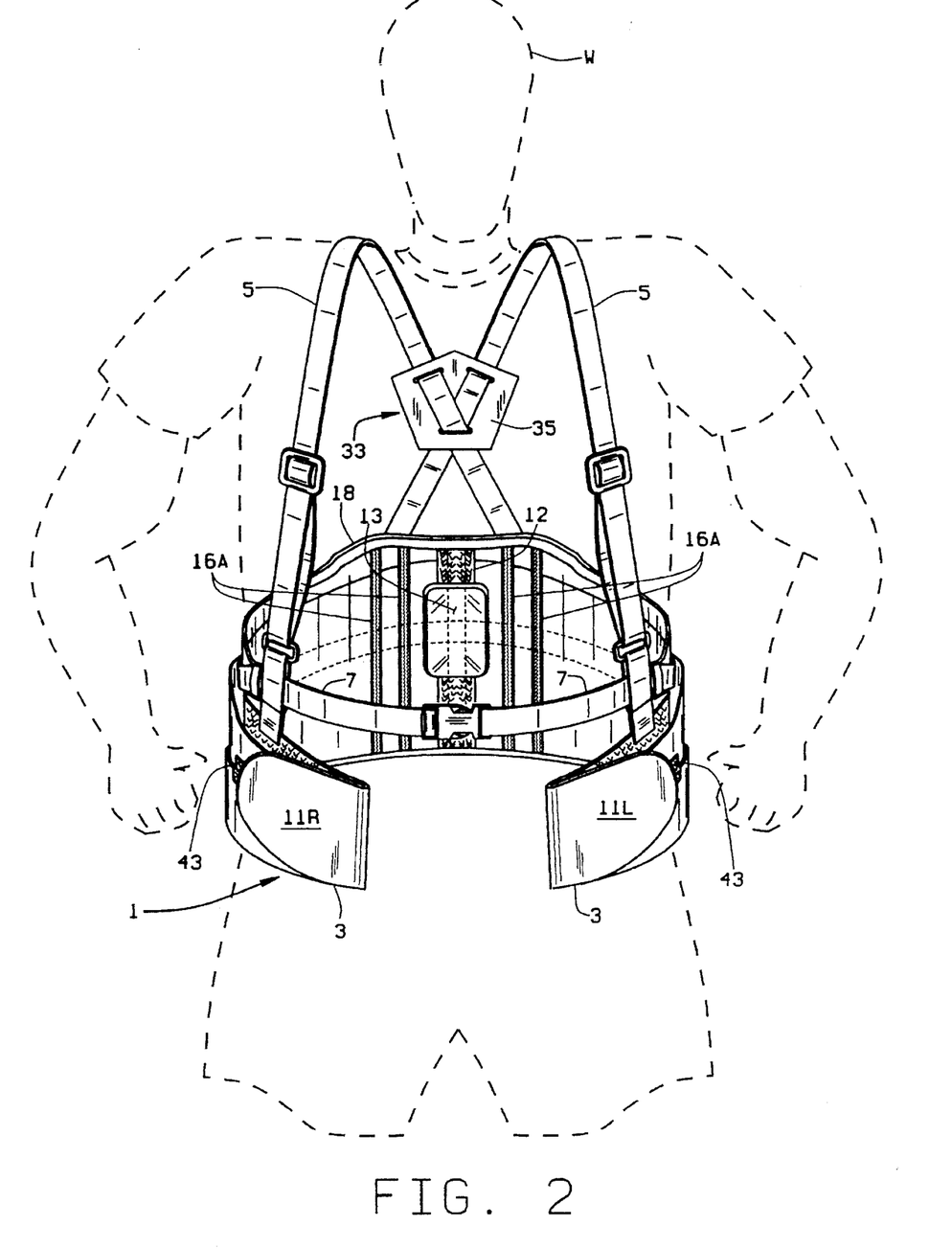
FIG. 2 is a perspective view of the back support of FIG. 1 in its open position.
Figure 3:
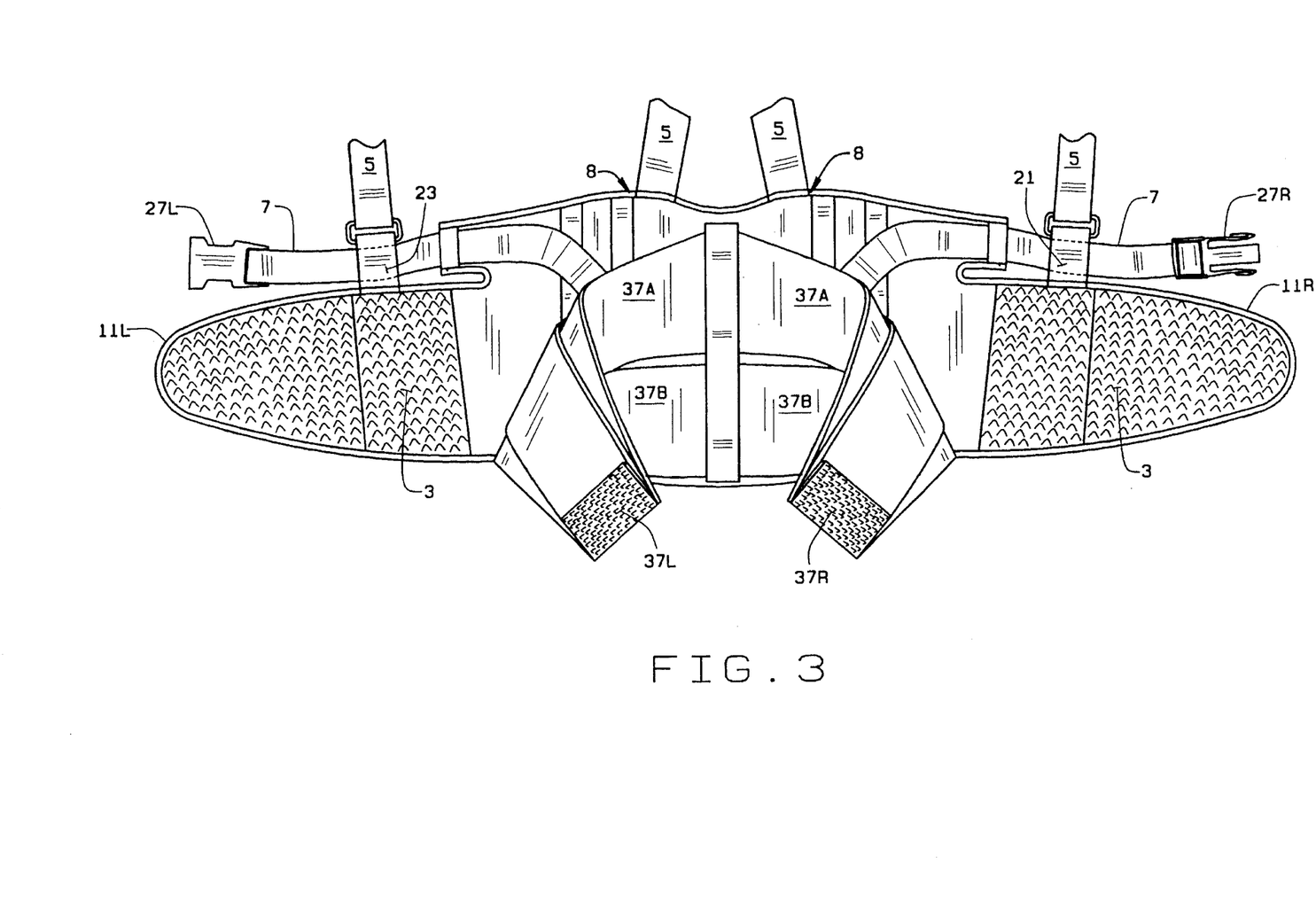
FIG. 3 is an exploded view of the back support of FIG. 1 from the rear.

Referring to FIGS. 1–3, reference numeral 1 represents an illustrative embodiment of a back support of the present invention. Back support 1 includes a support belt 3, shoulder strap or suspenders 5, and a secondary belt 7. Back support 1 is worn around the waist of a wearer "W" to provide support for the wearer's back. Suspenders 5 are connected to support belt 3 as shown at 6 on the left and right sides of the front portion of the belt and are connected to the back portion 3A of belt 3 as indicated at 8. The suspenders include a pair of loops 21 and 23 through which pass secondary belt 7.

Support belt 3 includes padded left and right free ends 11L and 11R. Both free ends have hook and pile fastener material secured to outer surfaces thereof. One of the free ends (free end 11L in FIG. 1) also has mating hook and pile fastener material secured to the inner surface thereof, which in combination with the corresponding fastener material of the other free end (free end 11R) is used by the wearer to removably secure belt 3 around the waist of the user.

Figure 4:
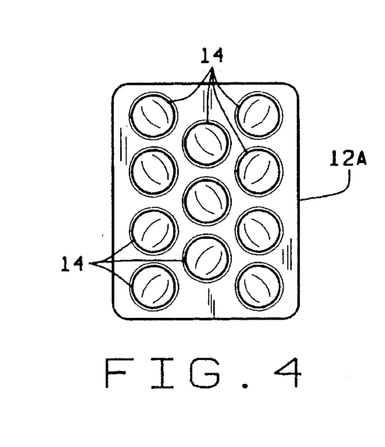
FIG. 4 is a front elevation of a back support pad used with the present invention.
Figure 5:
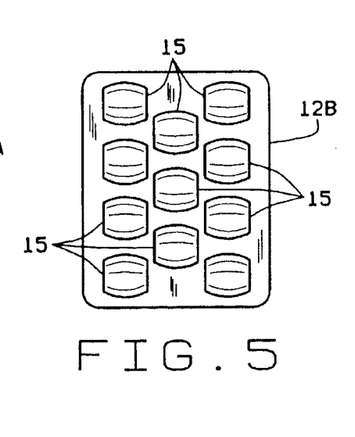
FIG. 5 is a front elevation of an alternative back support pad, similar to that of FIG. 4.
Figure 6:
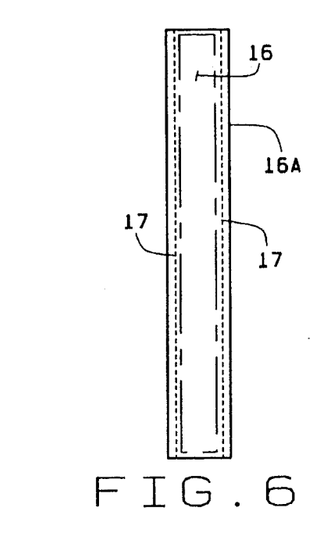
FIG. 6 is a front elevation of a stay pocket used on the back support of FIG. 1.
Figure 6A:
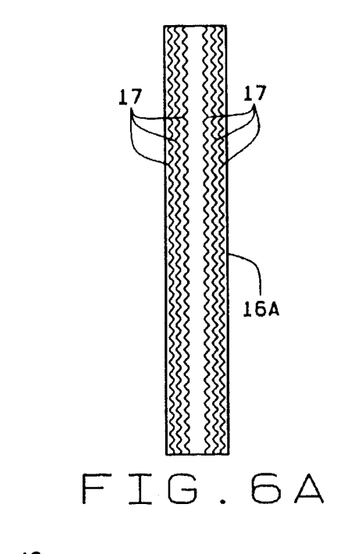
FIG. 6A is a view similar to FIG. 6 showing the external gripping surface formed on the stay pockets.

Belt 3 is narrowest at the free ends 11L and 11R and widens toward the back portion 3A. Back portion 3A includes a band 12 of hook and pile fastener material extending from the top to the bottom of the belt. Band 12 is used for removably securing a back pad 13 at a desired vertical position on belt 3 to provide additional lower back support for the wearer. It should be understood that although the back pad is shown as plain in FIGS. 1 and 2, it may be molded with a bead pattern 14 therein, or actually have beads 15 attached thereto (see FIGS. 4 and 5). Back portion 3A also includes a set of malleable stays 16 disposed in pockets 16A. The construction of the pockets is shown more clearly in FIG. 6. Pockets 16A are preferably of some pliable material such as plastic which is sewn onto belt 3 by stitches 17. As shown in FIG. 6A, it is preferred that the pockets 16A each have a series of raised gripping surfaces 17 disposed on their outer surfaces to prevent the support belt from slipping while in place on a user. These gripping surfaces extend vertically with respect to the belt and are transverse to the longitudinal axis of the belt. It is preferred that each pocket 16A have such raised surfaces to provide the desired protection against slipping of the belt.

Turning back to FIGS. 1–3, a binding 18 is disposed along the upper edge of belt 3. The binding is secured to belt 3 by a zig zag stitch which permits stretching of the binding with the belt.

Secondary belt 7 is made from a narrow, elongate piece of material which is secured to the back portion 3A of the support belt at the midpoint 10 thereof, and has free ends 25R and 25L shown removably secured together in FIGS. 1 and 2 by a pair of clasp halves 27R and 27L. Belt 7 passes through loops 21 and 23. The wearer uses clasp halves 27R, 27L to secure the free ends of secondary belt 7 together. The inner surface of secondary belt 7 has hook and pile fastener material disposed thereon, which mates with the corresponding hook and pile fastener material on support belt 3. This allows for adjustment of belt 7. Other methods of adjusting belt 7 may of course be used.

As noted above, secondary belt 7 passes through loops 21 and 23 of suspenders 5. The suspenders pass from those loops up and over the shoulders of the wearer. Preferably, shoulder straps or suspenders 5 cross-over as at 33 and have a body piece 35 which holds the shoulder straps together at the point of cross-over.

Support belt 3 further includes a cinch strap 37 which is secured to support belt 3 along the middle back portion 3A so that it is outside of belt 3. Cinch strap 37 has a right half free end 37R and a left half free end 37L. The cinch strap is preferably made out of a plurality of pieces of elastic to provide a wide strap which will provide added support for the wearer's back. For example, two pieces of elastic fabric 37A and 37B are shown in FIG. 1, although additional pieces could also be used. Each piece of elastic material is secured together at the free ends 37L and 37R of the cinch strap and is secured as by sewing to the back portion 3A of the support belt 3. Both the inner and outer surfaces of one free end of the cinch strap have hook and pile fasteners applied thereto. The other free end of the cinch strap has hook and pile fasteners applied thereto only on the inside so that the free ends of the cinch slip may be closed to provide back support to the wearer. The hook and pile fastener on the outside of the first half is provided in part so that the two halves of the cinch strap may be secured together when the cinch strap is used, if desired. The hook and pile fastener on the inner surfaces of the cinch strap also allows the cinch straps to be secured to the hook and pile fastener on the outer surfaces of their respective closure halves 11R and 11L.

When the cinch straps are not expanded, they do not cover the free ends of belt 3 (i.e., the cinch strap halves, when relaxed, are shorter than the closure halves). This leaves some of the hook and pile fastener of the closure halves exposed. A pair of hook and pile fastener squares 43 are secured to the elastic pieces 37A and 37B of cinch strap 37. The free ends of belt 3 can be folded back to be secured against squares 43 so that belt 3 may be worn in an open position as shown in FIG. 2. This is cooler and more comfortable for the wearer when the belt is not needed for support. When the belt 3 is worn in the open position, secondary belt 7 maintains the belt in position.

To don back support 1, cinch straps 37 are separated from belt 3. The support 1 is then slipped on like a vest. The shoulder straps should be adjusted so that belt 3 rests low on the wearer's hips. The secondary belt is then adjusted and secured so that it fits snugly across the wearer's stomach. When the belt is not needed for support, it can be folded over on itself using squares 43 and closure free ends 11L and 11R.

To close belt 3 for support during lifting, the free ends of belt 3 are removed from squares 43 and secured to each other as shown in FIG. 1. The cinch strap halves are each then extended and secured by hook and pile fasteners to the desired position with respect to belt 3. The further the cinch straps are extended, the greater the support provided by support 1 will be.

Figure 7:
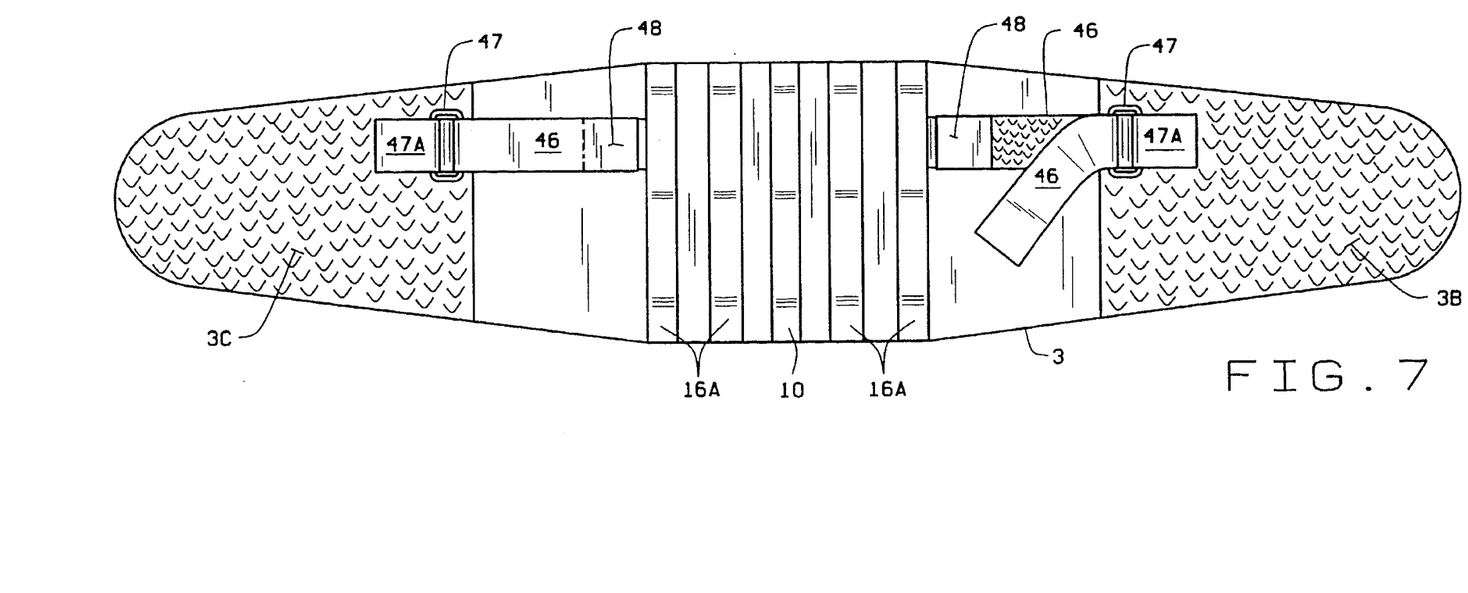
FIG. 7 is a rear view of an alternative back support of the present invention.

Turning to FIG. 7, an alternative embodiment of the present invention is shown. Belt 3 in this embodiment is shown without suspenders, although suspenders could be used if desired. This particular embodiment is provided to allow belt 3 to fit a multitude of body shapes. The particular modification allows the device to be tightened around hips and waist to provide a snug contoured fit. Belt 3 in this embodiment uses a pair of draw straps 46, one on each side of the transverse axis of the belt. Specifically, the straps are disposed one on each side of the midpoint 10 of the belt at the upper quadrant of the belt. Each strap is suitably attached, as by sewing, at one end to the nearest stay 16A. The other end of each strap is fed through a loop 47 which is in turn connected by means of a flap 47A to its respective belt panel 3B, 3C. The inner portion of each strap is covered with a pile fastener material, while a small segment 48 is covered with mating hook material. To adjust the belt to the individual user, the free end of each strap 46 is pulled the desired amount and the free end of the strap is then secured to corresponding hooked segment 48. Any excess amount of the strap may be cut off at that time. It should be appreciated that pulling the strap further than the positions shown in FIG. 7 results in darts being formed in the belt, which customizes the fit to the wearer. These darts allow the belt to readily accommodate curved body shapes.

Figure 7A:
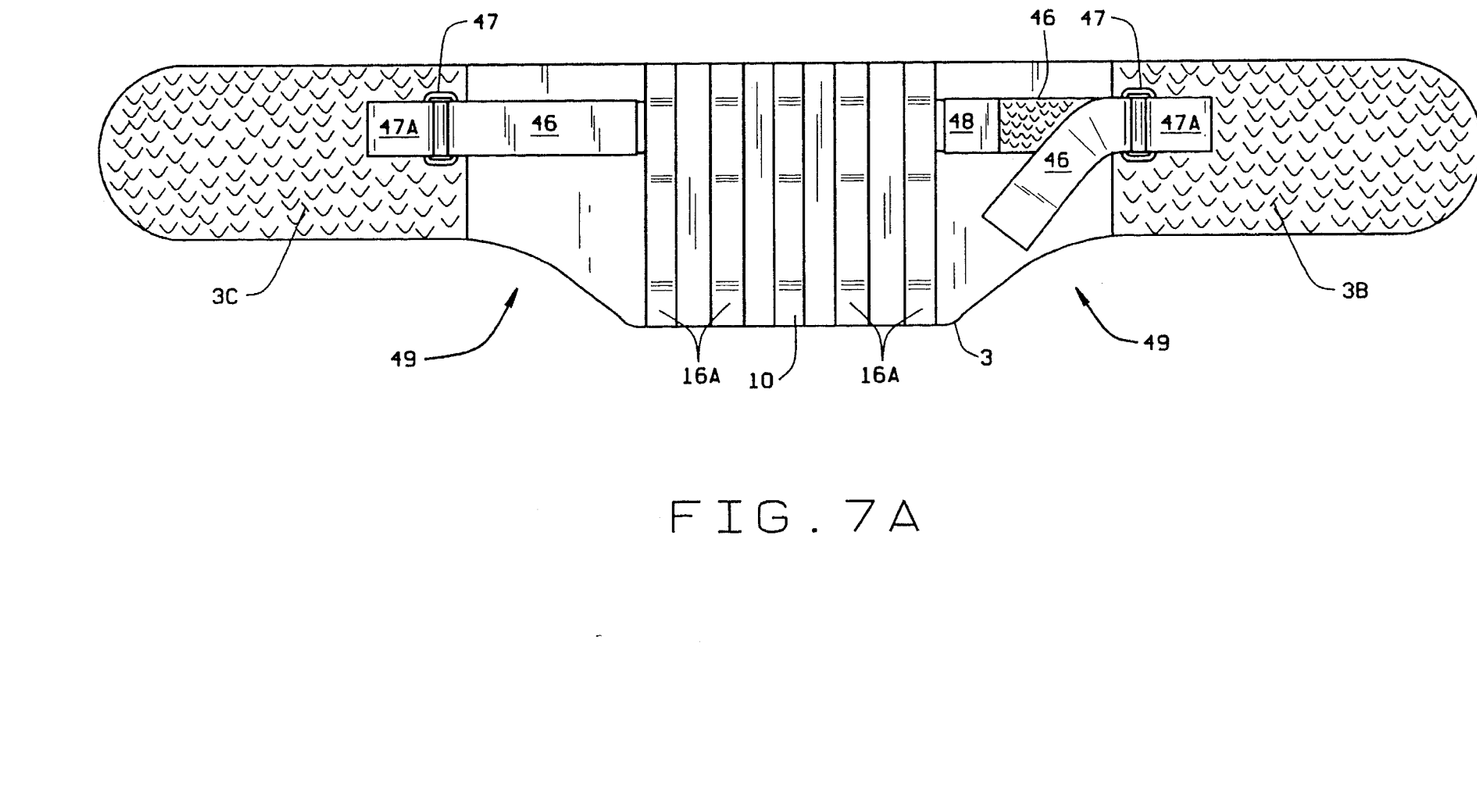
FIG. 7A is a view similar to FIG. 7 illustrating a modification to the back support of that FIG.

The belt 3 shown in FIG. 7A is similar to that shown in FIG. 7, but it also includes a pair of cut-outs 49 to prevent the belt from cutting into the legs of a wearer when the wearer assumes a sitting position.

Figure 8:
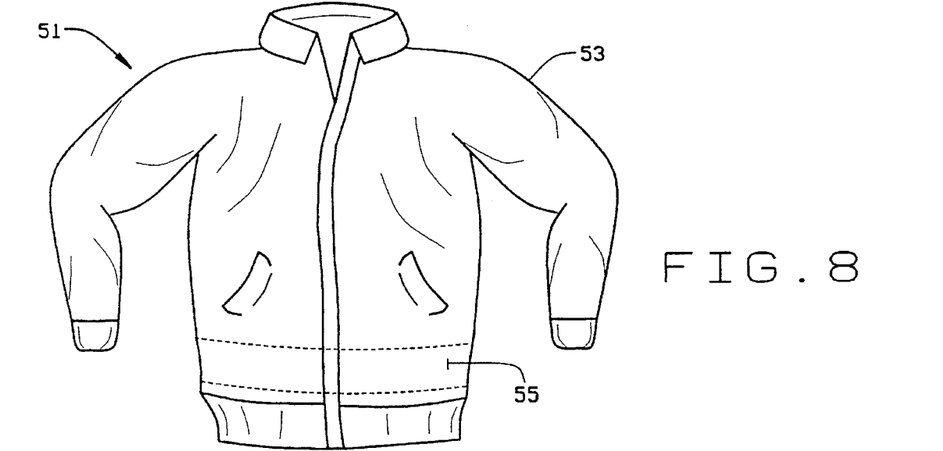
FIG. 8 is a front elevation of a back support garment of the present invention.

Turning to FIG. 8, a back support garment of the present invention is shown as a jacket or lab coat 51, although it is contemplated that any number of different garments could be used including a fireman's jacket, a tool vest, a truck driver's vest, a fisherman's vest, and similar garments. The garment 51 includes a garment body 53 having a garment front and a garment back defining an inside and an outside of the garment. The garment body is, in general, suitably sized for a torso of a human wearer. An elastic support belt 55 is disposed inside the garment body and secured thereto. As will become apparent, elastic support belt 55 is similar in most respects to back support 1 described above, except that the shoulder straps are not used since the garment itself holds the belt in place. Specifically, elastic support belt 55 has first and second free ends provided with hook and pile fasteners for releasably joining the free ends for maintaining the support belt in a closed position in which the support belt forms a closed surface adapted to encircle the human wearer as shown in FIG. 8.

Figure 9:
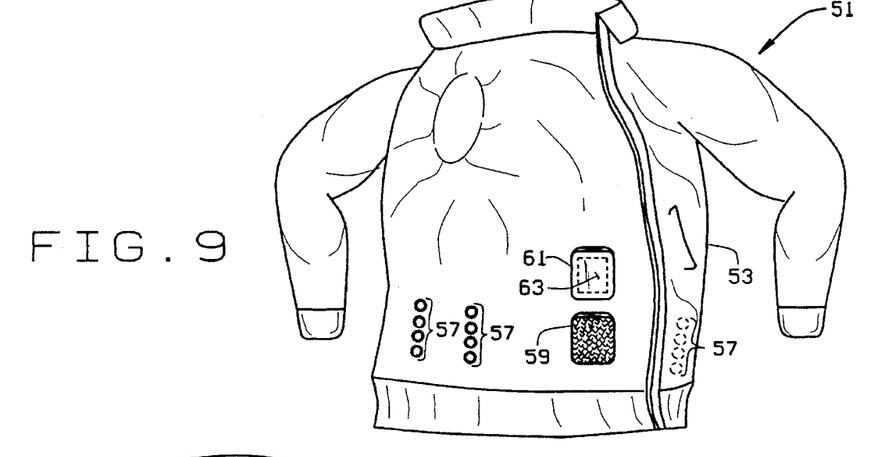
FIG. 9 is a view similar to FIG. 8 showing the garment partially folded back to reveal internal construction, with the support belt removed for clarity.

As can be seen in FIG. 9, garment 51 includes two sets of snaps 57 and a strip of hook and pile fastener material 59 which cooperate with corresponding structure on belt 55 to removably secure the elastic support belt to the front and back of the garment body. Although both snaps and hook and pile fasteners are shown, either could be used exclusively for the purpose of removably securing the belt to the garment, or other suitable fastening devices could be used as well. Note that the fastening devices are disposed so that the elastic support belt 55 may be secured at different relative positions with respect to the garment to vary the height of the support belt with respect to the garment body. Also shown in FIG. 9 is a pouch 61 for holding an upper back support pad 63, if desired.

Figure 10:
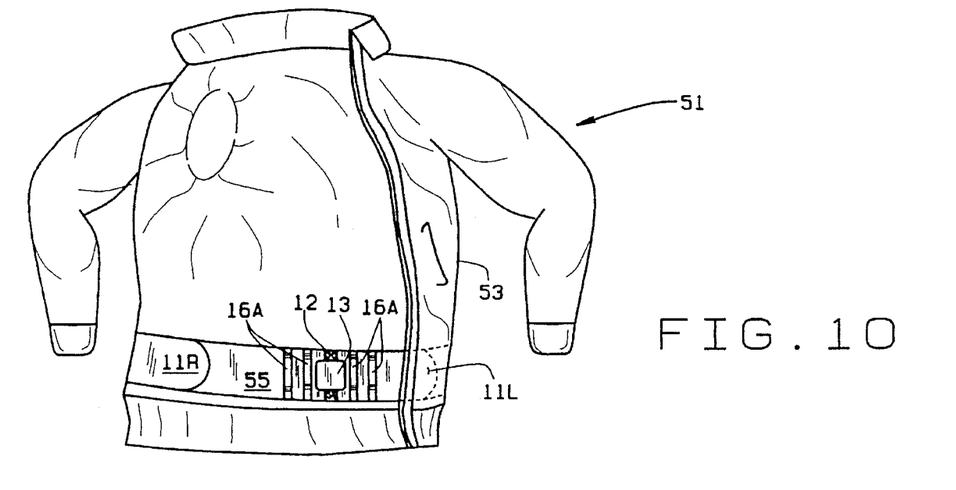
FIG. 10 is a view similar to FIG. 9 showing the support belt attached to the garment body in a rest position.

As shown most clearly in FIG. 10, the free ends 11L and 11R of the elastic support belt 55 are foldable back on themselves and preferably have hook and pile fastener material disposed thereon to releasably secure the free ends in the folded back position.

It is preferred that elastic support belt 55 include the lower back pad 13 described above in connection with belt 3 releasably secured thereto on the inner surface of belt 55 approximately at the mid-point between the free ends of the belt. Preferably lower back pad 13 is releasably secured to strip 12 of hook and pile fastener material so that it may be vertically adjusted with respect to the support belt as desired by the wearer. Similarly, belt 55 preferably includes the stretchable binding along the edge thereof described above in connection with belt 3, the malleable stays in stay pockets 16A, and the gripping surfaces 17 on the stay pockets. It is desired that the belt be attached to the back of the garment body in such a way that the garment body be allowed to move vertically somewhat without movement of the belt. That is, there is preferably some "give" at the point of attachment of the midpoint of the belt 55 to the garment body 53. This reduces any binding which might otherwise occur as the user moves his or her arms and shoulders.

Figure 11:
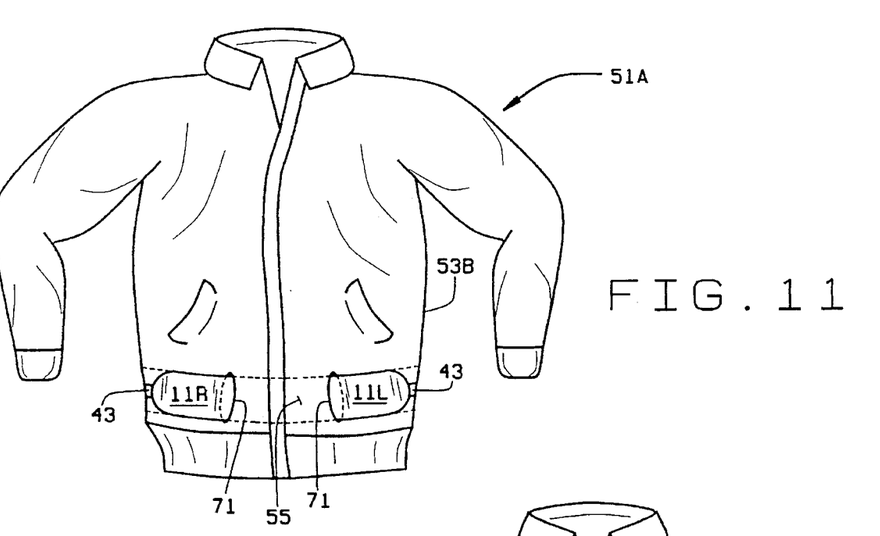
FIG. 11 is a front elevation of an alternative embodiment of the back support garment of FIG. 8 with the support belt in a rest position.
Figure 12:
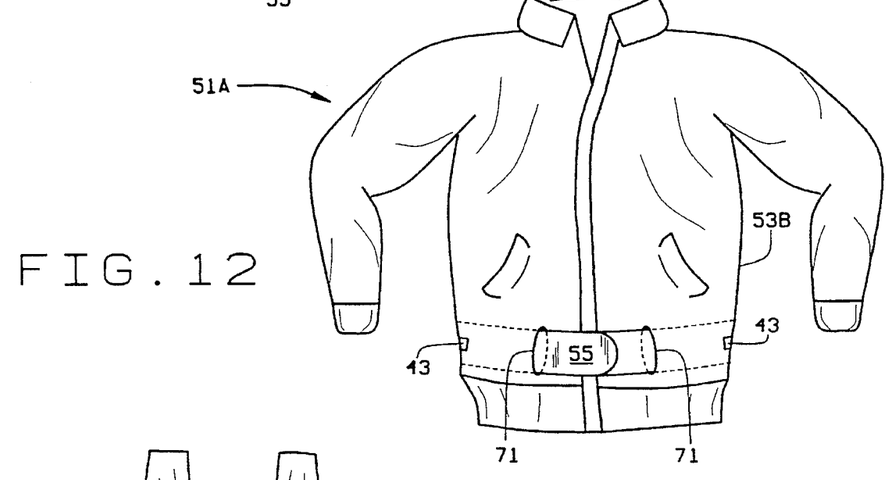
FIG. 12 is a view similar to FIG. 11 showing the support belt in the operative position.

Turning to FIGS. 11 and 12, there is shown an alternative garment 51A which differs from that of the previous FIGS. only in having a pair of slits 71 formed in the front thereof. Elastic support belt 55 passes through the slits so that the free ends may be releasably joined together on the outside of the garment as shown in FIG. 12. When not in use, the free ends are folded back and are releasably attached to hook and pile fastener squares 43 disposed on each side of the garment body.

Figure 13:
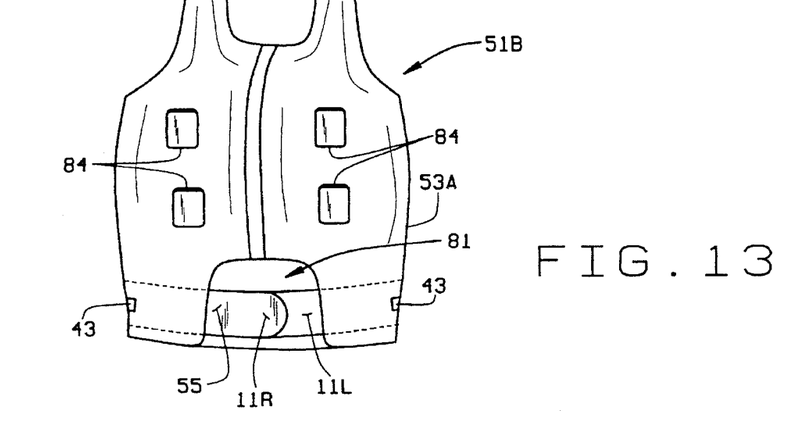
FIG. 13 is a front elevation of another back support garment of the present invention.

FIG. 13 shows a garment body 53A, such as a tool vest, truck driver's vest, hunter's vest, or fisherman's vest, used with elastic support belt 55. Such a vest may include the cut-out area 81 shown, which allows the wearer to cinch the belt tight without unbuttoning or unzipping the garment body. When not in use, the free ends 11L and 11R of the belt 55 may be folded back and releasably secured to hook and pile fastener squares 43, as described above. When used as a sporting vest such as for hunting or fishing, vest 53A preferably includes a plurality of pockets 84 for holding gear such as lures, ammunition, etc.

The forgoing description is set forth for illustrative purposes only. Numerous variations, within the scope of the claims, may be apparent to those skilled in the art. For example, snaps, rather than hook and pile fasteners may be used to close the belt 3 and to secure the cinch straps to the belt when the belt is being worn in its open position. Similarly, snaps may be used to hold the belt in its open position. These examples are merely illustrative.

What is claimed is:

1. A back support for a human user comprising an elastic support belt having first and second free ends, means secured to the support belt for releasably joining said free ends for maintaining said support belt in a closed position in which the support belt forms a closed surface adapted to encircle a human user, and means secured to the support belt for releasably maintaining said belt in an open position in which the support belt free ends are unattached to each other, said means for maintaining the back support in said open position including means for releasably securing said first free end to a point of the support belt spaced from the first free end and means for releasably securing said second free end to a point of the support belt spaced from the second free end.

2. The back support as set forth in claim 1 wherein said means for releasably securing said free ends to said support belt includes hook and pile fasteners.

3. A back support for a human user comprising an elastic support belt having first and second free ends, means secured to the support belt for releasably joining said free ends for maintaining said support belt in a closed position in which the support belt forms a closed surface adapted to encircle a human user, means secured to the support belt for releasably maintaining said belt in an open position in which the support belt free ends are unattached to each other, and a second belt for maintaining said support belt in place about a human user when said support belt is in its open position.

4. The back support as set forth in claim 3 further including loops attached to the support belt, said second belt being disposed to pass through said loops.

5. The back support as set forth in claim 4 wherein the second belt is fixedly secured to the support belt at a position spaced from the loops.

6. A back support for a human user comprising an elastic support belt having first and second free ends, means secured to the support belt for releasably joining said free ends for maintaining said support belt in a closed position in which the support belt forms a closed surface adapted to encircle a human user, and means secured to the support belt for releasably maintaining said belt in an open position in which the support belt free ends are unattached to each other, further including a lower back pad releasably secured to said support belt on an inner surface thereof and at approximately the midpoint between said free ends, means for vertically adjusting the back pad with respect to the support belt, said means for vertically adjusting said back pad including hook and pile fasteners which extend vertically along said midpoint of said belt, said back pad having beads secured thereto.

7. A back support for a human user comprising an elastic support belt having first and second free ends, means secured to the support belt for releasably joining said free ends for maintaining said support belt in a closed position in which the support belt forms a closed surface adapted to encircle a human user, and means secured to the support belt for releasably maintaining said belt in an open position in which the support belt free ends are unattached to each other, further including a lower back pad releasably secured to said support belt on an inner surface thereof and at approximately the midpoint between said free ends, means for vertically adjusting the back pad with respect to the support belt, said means for vertically adjusting said back pad including hook and pile fasteners which extend vertically along said midpoint of said belt, said back pad having a bead pattern formed therein.

8. A back support garment comprising:

a garment body having a garment front and a garment back defining an inside and an outside of the garment, said garment body being suitably sized for a torso of a human wearer;

an elastic support belt having first and second free ends and means secured to the support belt for releasably joining said free ends for maintaining the support belt in a closed position in which the support belt forms a closed surface adapted to encircle the human wearer, said free ends of the elastic support belt being foldable back on themselves, the elastic support belt further including means for releasably securing the free ends in the folded back position.

9. The back support garment as set forth in claim 8 wherein the means for releasably securing the free ends of the elastic support belt in the folded back position includes hook and pile fasteners.

10. The back support garment as set forth in claim 9 wherein the hook and pile fasteners are disposed in part on the inside of the elastic support belt.

11. A back support for a human user comprising an elastic support belt having first and second free ends, means secured to the support belt for releasably joining said free ends for maintaining said support belt in a closed position in which the support belt forms a closed surface adapted to encircle a human user, and means secured to the support belt for manually adjusting the effective length of the support belt along a longitudinal line spaced from the longitudinal axis of the belt so that the belt on one side of the longitudinal axis has an effective length shorter than the effective length on the other side of the longitudinal axis, the manually adjusting means including a pair of straps fixedly secured at one end to the belt, and removably securable at the other end to the belt such that the position of removable securement of the straps to the belt determines the effective length of the support belt along said longitudinal line.

12. The back support as set forth in claim 11 further including a pair of loops fixedly secured to the belt, each strap passing through a corresponding loop so that movement of the strap causes a corresponding change in the effective length of the belt along said longitudinal line.

13. A back support sport vest comprising:

a sport vest body having a vest front and a vest back defining an inside and an outside of the vest, said vest body being suitably sized for a torso of a human wearer;

an elastic support belt disposed inside the vest body and secured thereto, said elastic support belt having first and second free ends and means secured to the support belt for releasably joining said free ends for maintaining the support belt in a closed position in which the support belt forms a closed surface adapted to encircle the human wearer;

the sport vest body defining a cut-out in the vest front, said elastic support belt being disposed behind said cut-out for easy access thereto by the human wearer.

14. The back support sport vest as set forth in claim 13 further including means for releasably holding the free ends of the support belt separated when not in use, said releasably holding means being disposed to hold the free ends of the support belt on the outside of the vest.

\* \* \* \* \*